(12) United States Patent
Barthe

(10) Patent No.: US 8,858,471 B2
(45) Date of Patent: Oct. 14, 2014

(54) METHODS AND SYSTEMS FOR ULTRASOUND TREATMENT

(75) Inventor: Peter G. Barthe, Phoenix, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

(21) Appl. No.: 13/545,929

(22) Filed: Jul. 10, 2012

(65) Prior Publication Data

US 2013/0012842 A1 Jan. 10, 2013

Related U.S. Application Data

(60) Provisional application No. 61/506,125, filed on Jul. 10, 2011, provisional application No. 61/506,127, filed on Jul. 10, 2011, provisional application No. 61/506,126, filed on Jul. 10, 2011, provisional application No. 61/506,160, filed on Jul. 10, 2011, provisional application No. 61/506,163, filed on Jul. 10, 2011, provisional application No. 61/506,609, filed on Jul. 11, 2011, provisional application No. 61/506,610, filed on Jul. 11, 2011.

(51) Int. Cl.
*A61H 1/00* (2006.01)
*A61N 7/02* (2006.01)
*A61N 7/00* (2006.01)
*A61B 18/18* (2006.01)
*A61B 18/00* (2006.01)
*A61M 37/00* (2006.01)

(52) U.S. Cl.
CPC ............ *A61N 7/02* (2013.01); *A61N 2007/0034* (2013.01); *A61N 2007/0039* (2013.01); *A61N 2007/0017* (2013.01); *A61N 2007/0073* (2013.01); *A61B 18/18* (2013.01); *A61N 2007/0078* (2013.01); *A61N 2007/0052* (2013.01); *A61B 2018/00642* (2013.01); *A61N 2007/006* (2013.01); *A61M 37/0092* (2013.01); *A61N 2007/027* (2013.01)
USPC ................... 601/3; 601/2; 310/335; 600/437; 600/439

(58) Field of Classification Search
None
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

DE 4029175 3/1992
DE 10140064 3/2003
(Continued)

OTHER PUBLICATIONS

Chen, L. et al., "'Effect of Blood Perfusion on the ablation of liver perenchyma with high intensity focused ultrasound,'" Phys. Med. Biol; 38:1661-1673; 1993b.

(Continued)

*Primary Examiner* — Nicholas Evoy
(74) *Attorney, Agent, or Firm* — Michael J. Lang

(57) ABSTRACT

A method and system for ultrasound treatment are provided. Acoustic energy, including ultrasound, can serve as input energy to a mask with apertures, such apertures acting as secondary acoustic sources to create a modulated output acoustic energy in a treatment region and treatment effects. Under proper control output energy can be precisely placed and controlled in tissue. In some embodiments, methods and systems are configured for ultrasound treatment based on creating an output energy distribution in tissue. In some embodiments, methods and systems are configured based on creating an output temperature distribution in tissue.

18 Claims, 9 Drawing Sheets

(56) References Cited

U.S. PATENT DOCUMENTS

| | | | |
|---|---|---|---|
| 3,965,455 A * | 6/1976 | Hurwitz | 367/151 |
| 3,992,925 A | 11/1976 | Perilhou | |
| 4,039,312 A | 8/1977 | Patru | |
| 4,059,098 A | 11/1977 | Murdock | |
| 4,101,795 A | 7/1978 | Fukumoto | |
| 4,166,967 A | 9/1979 | Benes et al. | |
| 4,211,948 A | 7/1980 | Brisken et al. | |
| 4,211,949 A | 7/1980 | Brisken et al. | |
| 4,213,344 A | 7/1980 | Rose | |
| 4,276,491 A | 6/1981 | Daniel | |
| 4,315,514 A | 2/1982 | Drewes et al. | |
| 4,325,381 A | 4/1982 | Glenn | |
| 4,343,301 A | 8/1982 | Indech | |
| 4,372,296 A | 2/1983 | Fahim | |
| 4,379,145 A | 4/1983 | Masuho et al. | |
| 4,381,007 A | 4/1983 | Doss | |
| 4,381,787 A | 5/1983 | Hottinger | |
| 4,397,314 A | 8/1983 | Vaguine | |
| 4,409,839 A | 10/1983 | Tanezer | |
| 4,431,008 A | 2/1984 | Wanner et al. | |
| 4,441,486 A | 4/1984 | Pounds | |
| 4,452,084 A | 6/1984 | Taenzer | |
| 4,484,569 A | 11/1984 | Driller | |
| 4,507,582 A | 3/1985 | Glenn | |
| 4,513,749 A | 4/1985 | Kino | |
| 4,513,750 A | 4/1985 | Heyman et al. | |
| 4,527,550 A | 7/1985 | Ruggera et al. | |
| 4,528,979 A | 7/1985 | Marchenko | |
| 4,534,221 A | 8/1985 | Fife et al. | |
| 4,566,459 A | 1/1986 | Umemura et al. | |
| 4,567,895 A | 2/1986 | Putzke | |
| 4,586,512 A | 5/1986 | Do-Huu | |
| 4,601,296 A | 7/1986 | Yerushalmi | |
| 4,620,546 A | 11/1986 | Aida et al. | |
| 4,637,256 A | 1/1987 | Sugiyama et al. | |
| 4,646,756 A | 3/1987 | Watmough | |
| 4,663,358 A | 5/1987 | Hyon | |
| 4,668,516 A | 5/1987 | Duraffourd et al. | |
| 4,672,591 A | 6/1987 | Breimesser et al. | |
| 4,680,499 A | 7/1987 | Umemura et al. | |
| 4,697,588 A | 10/1987 | Reichenberger | |
| 4,754,760 A | 7/1988 | Fukukita et al. | |
| 4,757,820 A | 7/1988 | Itoh | |
| 4,771,205 A | 9/1988 | Mequio | |
| 4,801,459 A | 1/1989 | Liburdy | |
| 4,807,633 A | 2/1989 | Fry | |
| 4,817,615 A | 4/1989 | Fukukita et al. | |
| 4,858,613 A | 8/1989 | Fry | |
| 4,860,732 A | 8/1989 | Hasegawa et al. | |
| 4,865,041 A | 9/1989 | Hassler | |
| 4,865,042 A | 9/1989 | Umemura | |
| 4,867,169 A | 9/1989 | Machida | |
| 4,874,562 A | 10/1989 | Hyon | |
| 4,875,487 A | 10/1989 | Seppi | |
| 4,891,043 A | 1/1990 | Zeimer et al. | |
| 4,893,624 A | 1/1990 | Lele | |
| 4,896,673 A | 1/1990 | Rose | |
| 4,900,540 A | 2/1990 | Ryan et al. | |
| 4,901,729 A | 2/1990 | Saitoh et al. | |
| 4,917,096 A | 4/1990 | Englehart | |
| 4,973,096 A | 4/1990 | Jaworski | |
| 4,938,216 A | 7/1990 | Lele | |
| 4,938,217 A | 7/1990 | Lele | |
| 4,947,046 A | 8/1990 | Kawabata et al. | |
| 4,951,653 A | 8/1990 | Fry | |
| 4,955,365 A | 9/1990 | Fry | |
| 4,958,626 A | 9/1990 | Nambu | |
| 4,976,709 A | 12/1990 | Sand | |
| 4,979,501 A | 12/1990 | Valchanov | |
| 4,992,989 A | 2/1991 | Watanabe et al. | |
| 5,012,797 A | 5/1991 | Liang | |
| 5,018,508 A | 5/1991 | Fry et al. | |
| 5,030,874 A | 7/1991 | Saito et al. | |
| 5,036,855 A | 8/1991 | Fry | |
| 5,040,537 A | 8/1991 | Katakura | |
| 5,054,310 A | 10/1991 | Flynn | |
| 5,054,470 A | 10/1991 | Fry | |
| 5,070,879 A | 12/1991 | Herres | |
| 5,088,495 A | 2/1992 | Miyagawa | |
| 5,115,814 A | 5/1992 | Griffith | |
| 5,117,832 A | 6/1992 | Sanghvi | |
| 5,123,418 A | 6/1992 | Saurel | |
| 5,143,063 A | 9/1992 | Fellner | |
| 5,143,074 A | 9/1992 | Dory | |
| 5,149,319 A | 9/1992 | Unger | |
| 5,150,711 A | 9/1992 | Dory | |
| 5,150,714 A | 9/1992 | Green | |
| 5,152,294 A | 10/1992 | Mochizuki et al. | |
| 5,156,144 A | 10/1992 | Iwasaki | |
| 5,158,536 A | 10/1992 | Sekins | |
| 5,159,931 A | 11/1992 | Pini | |
| 5,163,421 A | 11/1992 | Bernstein | |
| 5,163,436 A | 11/1992 | Saitoh et al. | |
| 5,178,135 A | 1/1993 | Uchiyama et al. | |
| 5,190,518 A | 3/1993 | Takasu | |
| 5,190,766 A | 3/1993 | Ishihara | |
| 5,191,880 A | 3/1993 | McLeod | |
| 5,205,287 A | 4/1993 | Erbel et al. | |
| 5,209,720 A | 5/1993 | Unger | |
| 5,212,671 A | 5/1993 | Fujii et al. | |
| 5,215,680 A | 6/1993 | D'Arrigo | |
| 5,224,467 A | 7/1993 | Oku | |
| 5,230,334 A | 7/1993 | Klopotek | |
| 5,230,338 A | 7/1993 | Allen et al. | |
| 5,247,924 A | 9/1993 | Suzuki et al. | |
| 5,255,681 A | 10/1993 | Ishimura et al. | |
| 5,257,970 A | 11/1993 | Dougherty | |
| 5,265,614 A | 11/1993 | Hayakawa | |
| 5,267,985 A | 12/1993 | Shimada et al. | |
| 5,269,297 A | 12/1993 | Weng | |
| 5,282,797 A | 2/1994 | Chess | |
| 5,295,484 A | 3/1994 | Marcus | |
| 5,295,486 A | 3/1994 | Wollschlager et al. | |
| 5,304,169 A | 4/1994 | Sand | |
| 5,305,756 A | 4/1994 | Entrekin et al. | |
| 5,321,520 A | 6/1994 | Inga et al. | |
| 5,323,779 A | 6/1994 | Hardy et al. | |
| 5,327,895 A | 7/1994 | Hashimoto et al. | |
| 5,348,016 A | 9/1994 | Unger et al. | |
| 5,360,268 A | 11/1994 | Hayashi | |
| 5,370,121 A | 12/1994 | Reichenberger | |
| 5,371,483 A | 12/1994 | Bhardwaj | |
| 5,375,602 A | 12/1994 | Lancee et al. | |
| 5,379,773 A | 1/1995 | Hornsby | |
| 5,380,280 A | 1/1995 | Peterson | |
| 5,380,519 A | 1/1995 | Schneider et al. | |
| 5,383,917 A | 1/1995 | Desai et al. | |
| 5,391,140 A | 2/1995 | Schaetzle | |
| 5,391,197 A | 2/1995 | Burdette et al. | |
| 5,392,259 A | 2/1995 | Bolorforosh | |
| 5,396,143 A | 3/1995 | Seyed-Bolorforosh et al. | |
| 5,398,689 A | 3/1995 | Connor et al. | |
| 5,406,503 A | 4/1995 | Williams, Jr. et al. | |
| 5,417,216 A | 5/1995 | Tanaka | |
| 5,419,327 A | 5/1995 | Rohwedder | |
| 5,423,220 A | 6/1995 | Finsterwald et al. | |
| 5,435,311 A | 7/1995 | Umemura | |
| 5,438,998 A | 8/1995 | Hanafy | |
| 5,458,596 A | 10/1995 | Lax | |
| 5,460,179 A | 10/1995 | Okunuki et al. | |
| 5,460,595 A | 10/1995 | Hall et al. | |
| 5,469,854 A | 11/1995 | Unger et al. | |
| 5,471,988 A | 12/1995 | Fujio | |
| 5,487,388 A | 1/1996 | Rello et al. | |
| 5,492,126 A | 2/1996 | Hennige | |
| 5,496,256 A | 3/1996 | Bock | |
| 5,501,655 A | 3/1996 | Rolt | |
| 5,503,152 A | 4/1996 | Oakley et al. | |
| 5,503,320 A | 4/1996 | Webster et al. | |
| 5,507,790 A | 4/1996 | Weiss | |
| 5,520,188 A | 5/1996 | Hennige | |
| 5,522,869 A | 6/1996 | Burdette | |
| 5,523,058 A | 6/1996 | Umemura et al. | |
| 5,524,620 A | 6/1996 | Rosenschein | |

(56) References Cited

U.S. PATENT DOCUMENTS

| | | |
|---|---|---|
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A * | 9/1997 | Vago ................................ 95/30 |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A * | 8/1999 | Kline-Schoder et al. ..... 600/459 |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,984,882 A | 11/1999 | Rosenschein |
| 5,990,598 A | 11/1999 | Sudol et al. |
| 5,997,471 A | 12/1999 | Gumb et al. |
| 5,997,497 A | 12/1999 | Nita et al. |
| 6,004,262 A | 12/1999 | Putz et al. |
| 6,007,499 A | 12/1999 | Martin et al. |
| 6,013,032 A * | 1/2000 | Savord .......................... 600/443 |
| 6,016,255 A | 1/2000 | Bolan et al. |
| 6,022,327 A | 2/2000 | Chang |
| 6,036,646 A | 3/2000 | Barthe |
| 6,039,048 A | 3/2000 | Silberg |
| 6,042,556 A * | 3/2000 | Beach et al. ...................... 601/3 |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A * | 9/2000 | Klopotek .......................... 601/3 |
| 6,120,452 A | 9/2000 | Barthe |
| 6,123,081 A | 9/2000 | Durette |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |

(56) References Cited

U.S. PATENT DOCUMENTS

| | | |
|---|---|---|
| 6,325,758 B1 | 12/2001 | Carol et al. |
| 6,325,769 B1 * | 12/2001 | Klopotek .......................... 601/2 |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,572,552 B2 | 6/2003 | Fukukita |
| 6,575,956 B1 * | 6/2003 | Brisken et al. ................ 604/500 |
| 6,595,934 B1 | 7/2003 | Hissong |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,875,176 B2 | 4/2005 | Mourad |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,297,117 B2 | 11/2007 | Trucco et al. |
| 7,331,951 B2 | 2/2008 | Eshel et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 * | 7/2008 | Abend et al. .................. 600/450 |
| 7,491,171 B2 * | 2/2009 | Barthe et al. .................. 600/439 |
| 7,510,536 B2 * | 3/2009 | Foley et al. ........................ 601/2 |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 * | 11/2009 | Barthe et al. ....................... 601/3 |
| 7,695,437 B2 | 4/2010 | Quistgaard et al. |
| 7,758,524 B2 | 7/2010 | Barthe |
| 7,824,348 B2 | 11/2010 | Barthe et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,955,281 B2 | 6/2011 | Pedersen et al. |
| 7,967,764 B2 | 6/2011 | Lidgren et al. |
| 8,057,389 B2 | 11/2011 | Barthe et al. |
| 8,057,465 B2 | 11/2011 | Sliwa, Jr. et al. |
| 8,128,618 B2 | 3/2012 | Gliklich et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |

(56) References Cited

U.S. PATENT DOCUMENTS

| | | | |
|---|---|---|---|
| 8,409,097 B2 | 4/2013 | Slayton et al. | |
| 8,444,562 B2 | 5/2013 | Barthe et al. | |
| 8,480,585 B2 | 7/2013 | Slayton et al. | |
| 8,506,486 B2 | 8/2013 | Slayton et al. | |
| 8,523,775 B2 | 9/2013 | Barthe et al. | |
| 8,535,228 B2 | 9/2013 | Slayton et al. | |
| 8,585,618 B2 * | 11/2013 | Hunziker et al. | 601/2 |
| 2001/0009997 A1 | 7/2001 | Pope | |
| 2001/0009999 A1 | 7/2001 | Kaufman et al. | |
| 2001/0014780 A1 | 8/2001 | Martin et al. | |
| 2001/0014819 A1 | 8/2001 | Ingle et al. | |
| 2001/0031922 A1 | 10/2001 | Weng et al. | |
| 2001/0039380 A1 | 11/2001 | Larson et al. | |
| 2001/0041880 A1 | 11/2001 | Brisken | |
| 2002/0000763 A1 | 1/2002 | Jones | |
| 2002/0040199 A1 | 4/2002 | Klopotek | |
| 2002/0040442 A1 | 4/2002 | Ishidera | |
| 2002/0055702 A1 | 5/2002 | Atala | |
| 2002/0062077 A1 | 5/2002 | Emmenegger et al. | |
| 2002/0062142 A1 | 5/2002 | Knowlton | |
| 2002/0082528 A1 | 6/2002 | Friedman et al. | |
| 2002/0082589 A1 | 6/2002 | Friedman et al. | |
| 2002/0087080 A1 | 7/2002 | Slayton et al. | |
| 2002/0095143 A1 | 7/2002 | Key | |
| 2002/0128648 A1 | 9/2002 | Weber | |
| 2002/0143252 A1 | 10/2002 | Dunne et al. | |
| 2002/0156400 A1 | 10/2002 | Babaev | |
| 2002/0161357 A1 | 10/2002 | Anderson | |
| 2002/0165529 A1 | 11/2002 | Danek | |
| 2002/0168049 A1 | 11/2002 | Schriever | |
| 2002/0169394 A1 | 11/2002 | Eppstein et al. | |
| 2002/0169442 A1 | 11/2002 | Neev | |
| 2002/0173721 A1 | 11/2002 | Grunwald et al. | |
| 2002/0193831 A1 | 12/2002 | Smith | |
| 2003/0009153 A1 * | 1/2003 | Brisken et al. | 604/890.1 |
| 2003/0014039 A1 | 1/2003 | Barzell et al. | |
| 2003/0018255 A1 | 1/2003 | Martin | |
| 2003/0028113 A1 | 2/2003 | Gilbert et al. | |
| 2003/0032900 A1 | 2/2003 | Ella | |
| 2003/0036706 A1 | 2/2003 | Slayton et al. | |
| 2003/0040739 A1 | 2/2003 | Koop | |
| 2003/0050678 A1 | 3/2003 | Sierra | |
| 2003/0060736 A1 | 3/2003 | Martin et al. | |
| 2003/0065313 A1 | 4/2003 | Koop | |
| 2003/0074023 A1 | 4/2003 | Kaplan | |
| 2003/0083536 A1 | 5/2003 | Eshel | |
| 2003/0097071 A1 | 5/2003 | Halmann et al. | |
| 2003/0099383 A1 | 5/2003 | Lefebvre | |
| 2003/0125629 A1 | 7/2003 | Ustuner | |
| 2003/0139790 A1 | 7/2003 | Ingle et al. | |
| 2003/0171678 A1 | 9/2003 | Batten et al. | |
| 2003/0171701 A1 | 9/2003 | Babaev | |
| 2003/0176790 A1 | 9/2003 | Slayton | |
| 2003/0191396 A1 | 10/2003 | Sanghvi | |
| 2003/0200481 A1 | 10/2003 | Stanley | |
| 2003/0212129 A1 | 11/2003 | Liu et al. | |
| 2003/0212351 A1 | 11/2003 | Hissong | |
| 2003/0212393 A1 | 11/2003 | Knowlton | |
| 2003/0216795 A1 * | 11/2003 | Harth et al. | 607/88 |
| 2003/0220536 A1 | 11/2003 | Hissong | |
| 2003/0220585 A1 | 11/2003 | Hissong | |
| 2003/0229331 A1 * | 12/2003 | Brisken et al. | 604/500 |
| 2003/0233085 A1 | 12/2003 | Giammarusti | |
| 2003/0236487 A1 | 12/2003 | Knowlton | |
| 2004/0000316 A1 | 1/2004 | Knowlton | |
| 2004/0001809 A1 * | 1/2004 | Brisken et al. | 424/93.21 |
| 2004/0002705 A1 | 1/2004 | Knowlton | |
| 2004/0010222 A1 | 1/2004 | Nunomura et al. | |
| 2004/0015106 A1 | 1/2004 | Coleman | |
| 2004/0030227 A1 | 2/2004 | Littrup | |
| 2004/0039312 A1 | 2/2004 | Hillstead | |
| 2004/0039418 A1 | 2/2004 | Elstrom | |
| 2004/0042168 A1 | 3/2004 | Yang et al. | |
| 2004/0044375 A1 * | 3/2004 | Diederich et al. | 607/27 |
| 2004/0049134 A1 | 3/2004 | Tosaya et al. | |
| 2004/0059266 A1 | 3/2004 | Fry | |
| 2004/0073079 A1 | 4/2004 | Altshuler et al. | |
| 2004/0073113 A1 | 4/2004 | Salgo | |
| 2004/0073116 A1 | 4/2004 | Smith | |
| 2004/0073204 A1 | 4/2004 | Ryan et al. | |
| 2004/0077977 A1 | 4/2004 | Ella et al. | |
| 2004/0082857 A1 | 4/2004 | Schonenberger et al. | |
| 2004/0082859 A1 | 4/2004 | Schaer | |
| 2004/0102697 A1 | 5/2004 | Evron | |
| 2004/0105559 A1 | 6/2004 | Aylward et al. | |
| 2004/0122493 A1 | 6/2004 | Ishbashi et al. | |
| 2004/0143297 A1 | 7/2004 | Ramsey | |
| 2004/0152982 A1 | 8/2004 | Hwang et al. | |
| 2004/0186535 A1 | 9/2004 | Knowlton | |
| 2004/0189155 A1 | 9/2004 | Funakubo | |
| 2004/0206365 A1 | 10/2004 | Knowlton | |
| 2004/0210214 A1 | 10/2004 | Knowlton | |
| 2004/0217675 A1 | 11/2004 | Desilets | |
| 2004/0249318 A1 | 12/2004 | Tanaka | |
| 2004/0254620 A1 * | 12/2004 | Lacoste et al. | 607/96 |
| 2004/0267252 A1 | 12/2004 | Washington et al. | |
| 2005/0033201 A1 | 2/2005 | Takahashi | |
| 2005/0033316 A1 | 2/2005 | Kertz | |
| 2005/0055073 A1 | 3/2005 | Weber | |
| 2005/0061834 A1 | 3/2005 | Garcia et al. | |
| 2005/0070961 A1 | 3/2005 | Maki et al. | |
| 2005/0074407 A1 | 4/2005 | Smith | |
| 2005/0080469 A1 | 4/2005 | Larson | |
| 2005/0091770 A1 | 5/2005 | Mourad et al. | |
| 2005/0113689 A1 | 5/2005 | Gritzky | |
| 2005/0137656 A1 | 6/2005 | Malak | |
| 2005/0143677 A1 | 6/2005 | Young et al. | |
| 2005/0154313 A1 | 7/2005 | Desilets | |
| 2005/0154314 A1 | 7/2005 | Quistgaard | |
| 2005/0154332 A1 | 7/2005 | Zanelli | |
| 2005/0154431 A1 | 7/2005 | Quistgaard | |
| 2005/0187495 A1 | 8/2005 | Quistgaard | |
| 2005/0191252 A1 | 9/2005 | Mitsui | |
| 2005/0193451 A1 | 9/2005 | Quistgaard et al. | |
| 2005/0197681 A1 * | 9/2005 | Barolet et al. | 607/86 |
| 2005/0228281 A1 | 10/2005 | Nefos | |
| 2005/0240170 A1 | 10/2005 | Zhang et al. | |
| 2005/0256406 A1 | 11/2005 | Barthe | |
| 2005/0261584 A1 | 11/2005 | Eshel | |
| 2005/0261585 A1 | 11/2005 | Makin et al. | |
| 2005/0267454 A1 | 12/2005 | Hissong | |
| 2005/0288748 A1 | 12/2005 | Li et al. | |
| 2006/0004306 A1 * | 1/2006 | Altshuler et al. | 601/3 |
| 2006/0020260 A1 | 1/2006 | Dover et al. | |
| 2006/0025756 A1 | 2/2006 | Francischelli | |
| 2006/0042201 A1 | 3/2006 | Curry | |
| 2006/0058664 A1 | 3/2006 | Barthe | |
| 2006/0058671 A1 | 3/2006 | Vitek et al. | |
| 2006/0058707 A1 | 3/2006 | Barthe | |
| 2006/0058712 A1 * | 3/2006 | Altshuler et al. | 601/15 |
| 2006/0074309 A1 | 4/2006 | Bonnefous | |
| 2006/0074313 A1 | 4/2006 | Slayton et al. | |
| 2006/0074314 A1 | 4/2006 | Slayton | |
| 2006/0074355 A1 | 4/2006 | Slayton | |
| 2006/0079816 A1 * | 4/2006 | Barthe et al. | 601/2 |
| 2006/0079868 A1 | 4/2006 | Makin | |
| 2006/0084891 A1 | 4/2006 | Barthe | |
| 2006/0089632 A1 * | 4/2006 | Barthe et al. | 606/27 |
| 2006/0089688 A1 | 4/2006 | Panescu | |
| 2006/0094988 A1 | 5/2006 | Tosaya et al. | |
| 2006/0111744 A1 | 5/2006 | Makin | |
| 2006/0116671 A1 | 6/2006 | Slayton | |
| 2006/0122508 A1 | 6/2006 | Slayton | |
| 2006/0122509 A1 | 6/2006 | Desilets | |
| 2006/0161062 A1 | 7/2006 | Arditi et al. | |
| 2006/0184069 A1 | 8/2006 | Vaitekunas | |
| 2006/0184071 A1 * | 8/2006 | Klopotek | 601/2 |
| 2006/0189972 A1 | 8/2006 | Grossman | |
| 2006/0206105 A1 | 9/2006 | Chopra | |
| 2006/0229514 A1 | 10/2006 | Wiener | |
| 2006/0241440 A1 | 10/2006 | Eshel | |
| 2006/0241442 A1 * | 10/2006 | Barthe et al. | 600/439 |
| 2006/0241470 A1 | 10/2006 | Novak et al. | |
| 2006/0250046 A1 | 11/2006 | Koizumi et al. | |

(56) References Cited

U.S. PATENT DOCUMENTS

| | | |
|---|---|---|
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1* | 9/2007 | Yaroslavsky et al. ......... 607/100 |
| 2007/0219605 A1* | 9/2007 | Yaroslavsky et al. ......... 607/100 |
| 2007/0238994 A1* | 10/2007 | Stecco et al. ................... 600/437 |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1* | 1/2008 | Klopotek et al. ............. 600/472 |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pedersen |
| 2008/0139974 A1 | 6/2008 | Da Silva |
| 2008/0146970 A1* | 6/2008 | Litman et al. ...................... 601/2 |
| 2008/0167556 A1 | 7/2008 | Thompson et al. |
| 2008/0188745 A1 | 8/2008 | Chen et al. |
| 2008/0200810 A1* | 8/2008 | Buchalter ...................... 600/459 |
| 2008/0200813 A1 | 8/2008 | Quistgaard |
| 2008/0214966 A1 | 9/2008 | Slayton |
| 2008/0221491 A1* | 9/2008 | Slayton et al. ...................... 601/3 |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1* | 11/2008 | Barthe et al. ...................... 601/3 |
| 2008/0319356 A1 | 12/2008 | Cain et al. |
| 2009/0043198 A1* | 2/2009 | Milner et al. .................. 600/437 |
| 2009/0043293 A1 | 2/2009 | Pankratov et al. |
| 2009/0069677 A1 | 3/2009 | Chen et al. |
| 2009/0093737 A1* | 4/2009 | Chomas et al. ...................... 601/2 |
| 2009/0171252 A1 | 7/2009 | Bockenstedt et al. |
| 2009/0182231 A1* | 7/2009 | Barthe et al. .................. 600/439 |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0318909 A1 | 12/2009 | Debenedictis et al. |
| 2010/0011236 A1 | 1/2010 | Barthe et al. |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0160782 A1 | 6/2010 | Slayton et al. |
| 2010/0160837 A1* | 6/2010 | Hunziker et al. .................. 601/2 |
| 2010/0168576 A1 | 7/2010 | Poland et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0072826 A1 | 3/2013 | Slayton et al. |
| 2013/0096471 A1 | 4/2013 | Slayton et al. |
| 2013/0281853 A1 | 10/2013 | Slayton et al. |
| 2013/0281891 A1 | 10/2013 | Slayton et al. |
| 2013/0296700 A1 | 11/2013 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1374944 A | 1/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2007505793 A | 3/2007 |
| JP | 2009518126 | 5/2009 |
| JP | 2010517695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | 9735518 | 10/1997 |
| WO | 9832379 | 7/1998 |
| WO | 9933520 | 7/1999 |
| WO | 9949788 | 10/1999 |

(56) References Cited

FOREIGN PATENT DOCUMENTS

| | | |
|---|---|---|
| WO | 0006032 | 2/2000 |
| WO | 0015300 | 3/2000 |
| WO | 0021612 | 4/2000 |
| WO | 0053113 | 9/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 0224050 | 3/2002 |
| WO | 02092168 A | 11/2002 |
| WO | 02292168 | 11/2002 |
| WO | 03053266 A | 7/2003 |
| WO | 03065347 | 8/2003 |
| WO | 03070105 | 8/2003 |
| WO | 03077833 | 8/2003 |
| WO | 03086215 | 10/2003 |
| WO | 03096883 | 11/2003 |
| WO | 03099177 | 12/2003 |
| WO | 03101530 | 12/2003 |
| WO | 04000116 A | 12/2003 |
| WO | 2004080147 | 9/2004 |
| WO | 2004110558 | 12/2004 |
| WO | 2005065408 | 7/2005 |
| WO | 2005090978 | 9/2005 |
| WO | 2006036870 | 4/2006 |
| WO | 2006042168 | 4/2006 |
| WO | 2006042201 | 4/2006 |
| WO | 2006065671 | 6/2006 |
| WO | 2006082573 | 8/2006 |
| WO | 2007067563 A | 6/2007 |
| WO | 2008036622 A | 3/2008 |
| WO | 2009013729 | 1/2009 |

OTHER PUBLICATIONS

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Arthur et al., "Non-invasive estimation of hyperthermia temperatures with ultrasound," Int. J. Hyperthermia, Sep. 2005, 21(6), pp. 589-600.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Mitragotri, Samir; "Healing sound: the use of ultrasound in drug delivery and other therapeutic applications," Nature Reviews; Drug Delivery, pp. 255-260, vol. 4.

Sanghvi, N.T., et al., "Transrectal Ablation of Prostate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

(56) References Cited

OTHER PUBLICATIONS

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

European Examination Report in related Application No. 05808908.7 dated Jun. 29, 2009.

European Examination Report in related Application No. 05810308.6 dated Jun. 29, 2009.

European Examination Report in related Application No. 10185100.4 dated Jan. 6, 2014.

European Examination Report in related Application No. 10185120.2 dated Jan. 22, 2014.

Decision of the Korean Intellectual Property Tribunal dated Jun. 28, 2013 regarding Korean Patent No. 10-1142108, which is related to the pending application and/or an application indentified in the Table of the pp. 2-5 of the information Disclosure Statement herein (English translation, English translation certification, and Korean decision included).

International Search Report and Written Opinion dated Jan. 23, 2014 in Application No. PCT/US2012/046122.

International Search Report and Written Opinion dated Jan. 23, 2014 in Application No. PCT/US2012/046123.

International Search Report and Written Opinion dated Jan. 28, 2012 in Application No. PCT/US2012/046327.

International Search Report and Written Opinion dated Jan. 28, 2013 in Application No. PCT/US2012/046125.

International Search Report and Written Opinion dated Feb. 14, 2013 in Application No. PCT/US2011/001361.

International Search Report and Written Opinion dated Feb. 14, 2013 in Application No. PCT/US2011/001362.

International Search Report and Written Opinion dated Feb. 14, 2013 in Application No. PCT/US2011/001366.

International Search Report and Written Opinion dated Apr. 6, 2012 in Application No. PCT/US2011/001367.

\* cited by examiner $$\mathbb{I}(x,y,z,t) \Rightarrow \mathcal{M}(x,y,z,t) \Rightarrow \mathbb{O}(x,y,z,t)$$

METHODS AND SYSTEMS FOR ULTRASOUND TREATMENT

CROSS-REFERENCE TO RELATED APPLICATIONS

This application claims priority to and the benefit of U.S. Provisional Patent Application Ser. No. 61/506,125, entitled "Systems and Methods for Creating Shaped Lesions" filed Jul. 10, 2011; U.S. Provisional Patent Application Ser. No. 61/506,127, entitled "Systems and Methods for Treating Injuries to Joints and Connective Tissue," filed Jul. 10, 2011; U.S. Provisional Patent Application Ser. No. 61/506,126, entitled "System and Methods for Accelerating Healing of Implanted Materials and/or Native Tissue," filed Jul. 10, 2011; U.S. Provisional Patent Application Ser. No. 61/506,160, entitled "Systems and Methods for Cosmetic Rejuvenation," filed Jul. 10, 2011; U.S. Provisional Patent Application Ser. No. 61/506,163, entitled "Methods and Systems for Ultrasound Treatment," filed Jul. 10, 2011; U.S. Provisional Patent Application Ser. No. 61/506,609, entitled "Systems and Methods for Monitoring Ultrasound Power Efficiency," filed Jul. 11, 2011; and U.S. Provisional Patent Application Ser. No. 61/506,610, entitled "Methods and Systems for Controlling Acoustic Energy Deposition into a Medium," filed Jul. 11, 2011; all of which are incorporated by reference herein.

BACKGROUND

A variety of methods and systems and methods exist to treat tissue, including mechanical means, lasers and other photon-based sources, radio frequency (RF) electrical currents, microwaves, cryogenic based techniques, and their various combinations, among others.

Each of these modalities has limitations which prevent a high degree of spatial control and precision during treatment. For example, in tissue the extreme absorption and scattering of photons relegates light based therapies to superficial applications that are tissue specific. Typically, electric currents, such as those emitted from a RF source, flow along the path of least impedance and are diffuse and non-selective, with maximum effect to tissue at the source. Further, the centimeter wavelengths of microwaves preclude tight focusing and energy placement in tissue.

Ultrasound can provide depth and precision of energy placement in tissue; however, it has currently been limited in application to either broad planar sources such as used in physiotherapy treatment, or as a single beam of focused sound, which is scanned sequentially over numerous areas, either electronically or mechanically, which is slow. Array based systems which can produce multiple sound beams are cumbersome and expensive and cannot in general produce output energy with a high degree of control or flexibility.

What is needed is an ultrasound treatment method and system that can provide simultaneous multiple beams of controlled energy to produce fractionated intense energy effects, such as thermal effects.

SUMMARY

Methods and systems for ultrasound treatment are provided. Acoustic energy, including ultrasound, under proper functional control can penetrate deeply and be controlled precisely in tissue. In various embodiments, methods and systems can be configured for ultrasound treatment based on creating an input energy distribution, passing it through apertures in a mask, which act in parallel as secondary acoustic sources to create an output distribution function. In various embodiments, methods and systems can be configured to create and control a desired temperature distribution.

Some embodiments provide an ultrasound treatment system configured for temporarily or permanently affecting tissue or its physiology. The ultrasound treatment system can comprise an energy source configured for delivery of acoustic or other energy to a treatment region; a control system for facilitating control of the energy source; and a set of masks, apertures, mask components, input/output, and secondary systems in communication with the control system to define a spatio-temporal distribution of the energy in the treatment region.

Some embodiments provide a method for providing ultrasound treatment. The method can comprise localizing a treatment region; delivering acoustic energy from an energy source into the treatment region; controlling the delivery of acoustic energy; producing at least one treatment effect in the treatment region of interest with the delivering acoustic energy. The method can further comprise monitoring of results of the ultrasound treatment during and/or after of the delivery of acoustic energy. The method can further comprise planning of additional treatment.

DRAWINGS

The present disclosure will become more fully understood from the description and the accompanying drawings, wherein.

Figure 2A:
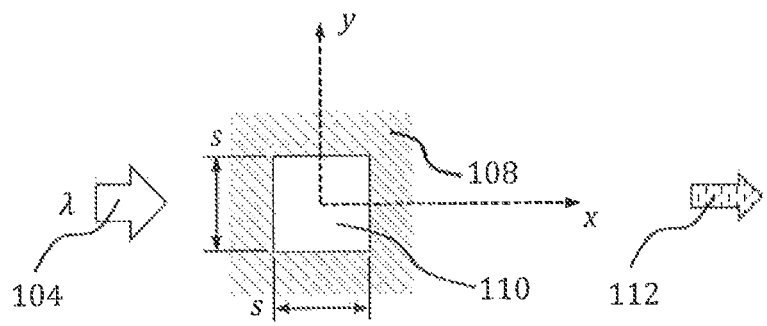
FIG. 2A is a diagram illustrating an ultrasound treatment system mask, in accordance with various non-limiting embodiments.
Figure 2B:
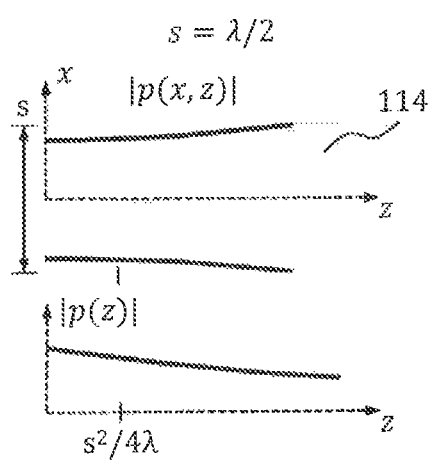
Figure 2C:
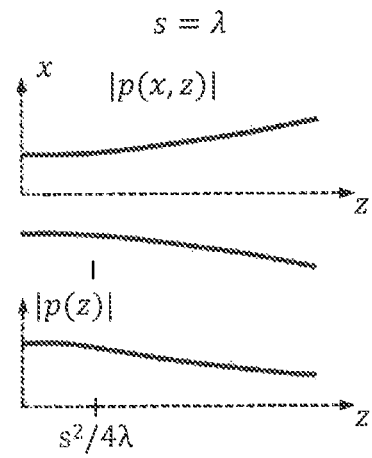
Figure 2D:
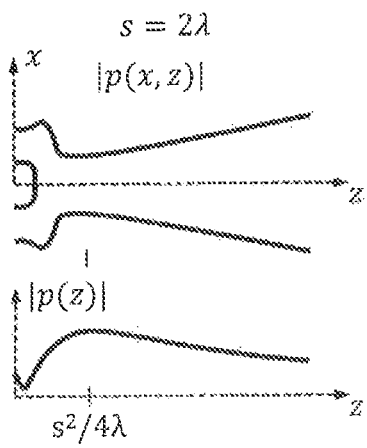
Figure 2E:
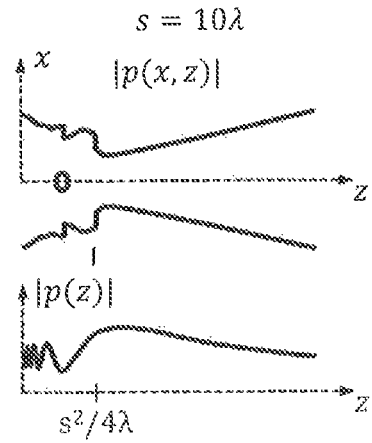
Figure 2F:
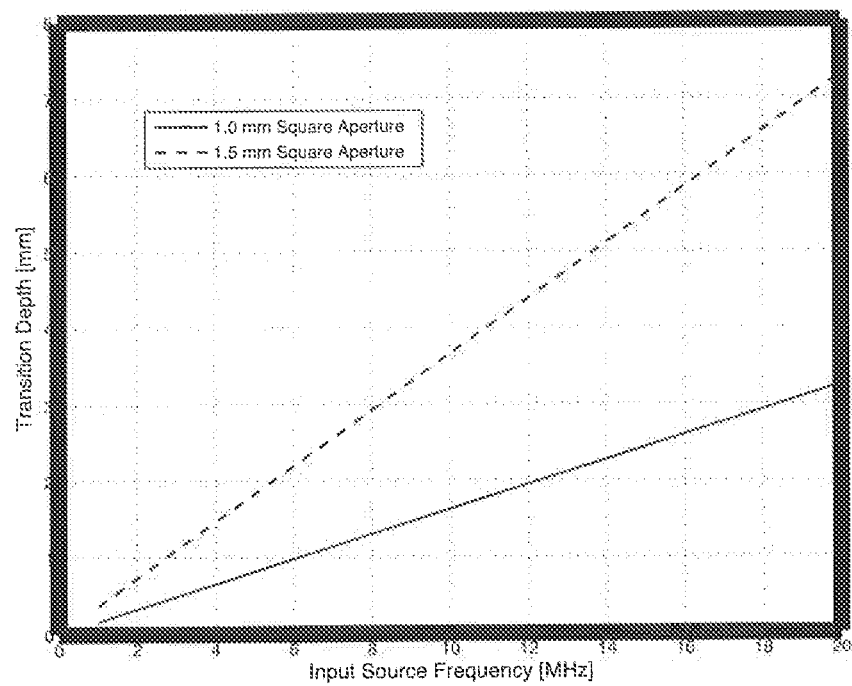
Figure 3:
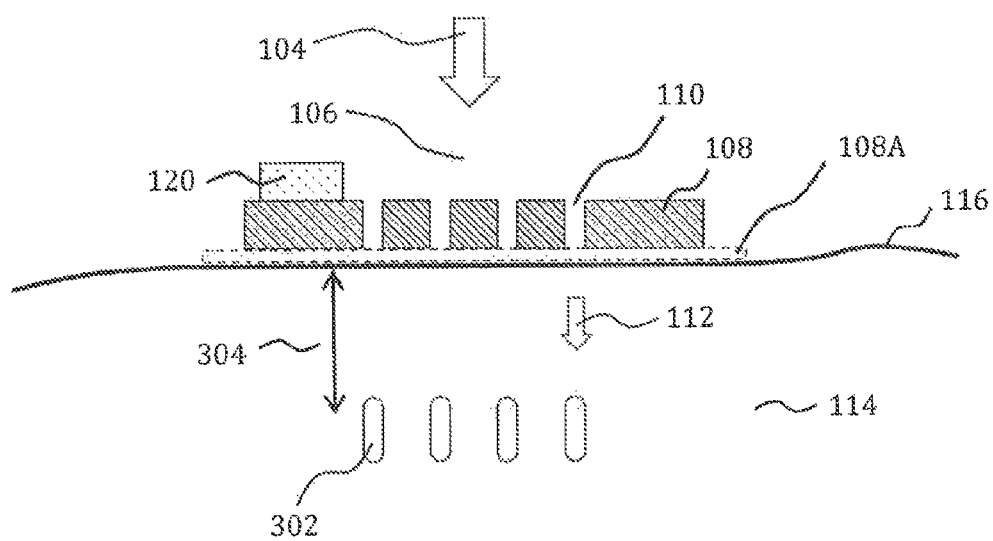
Figure 4:
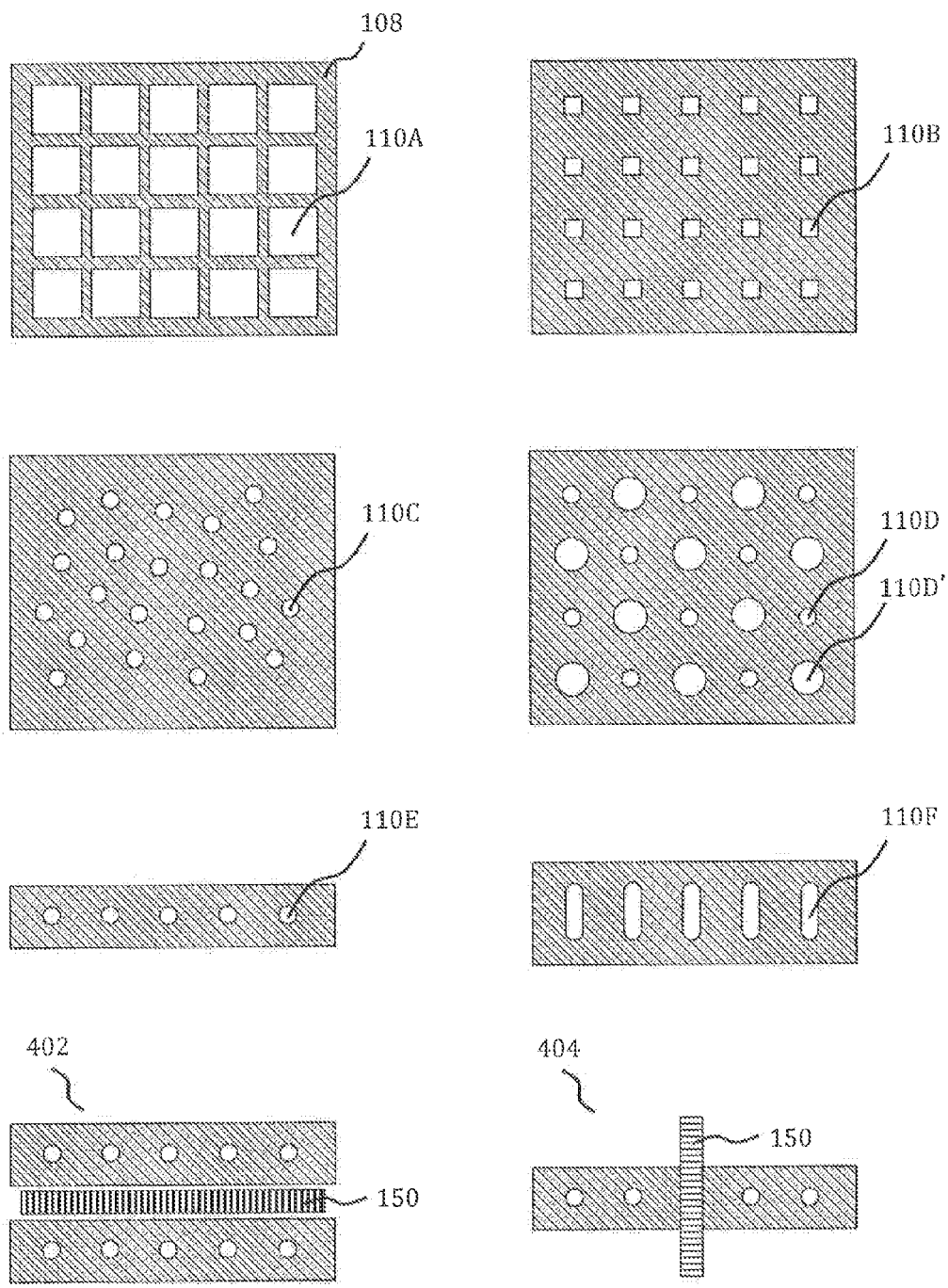
Figure 5:
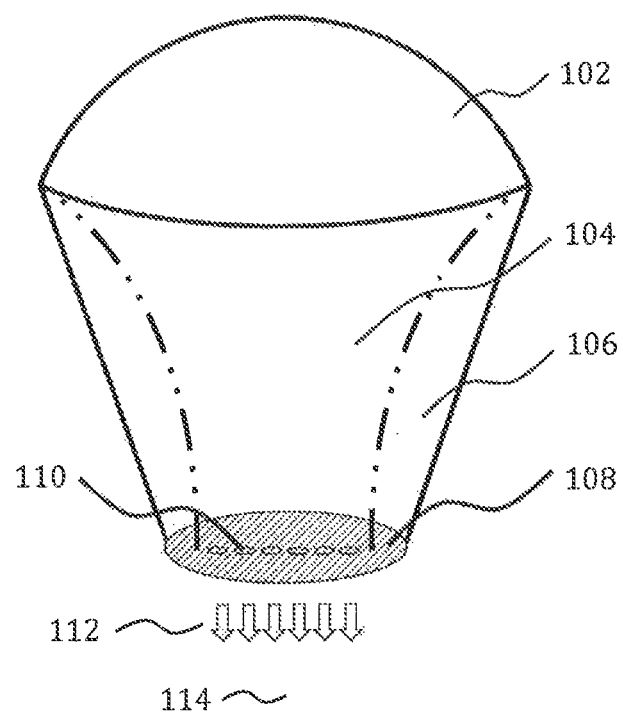
Figure 6:
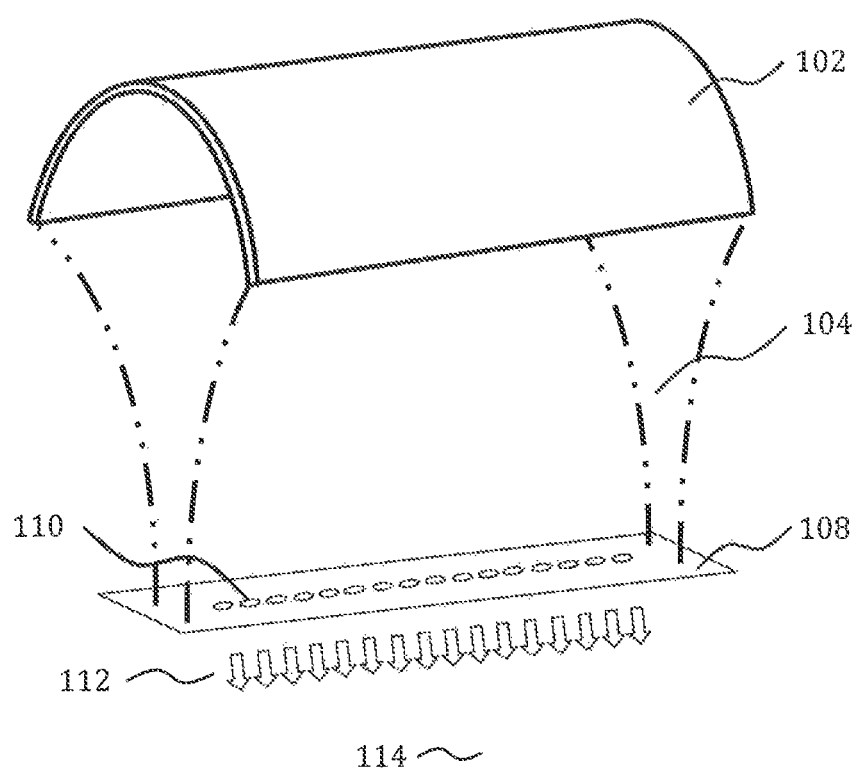
Figure 7:
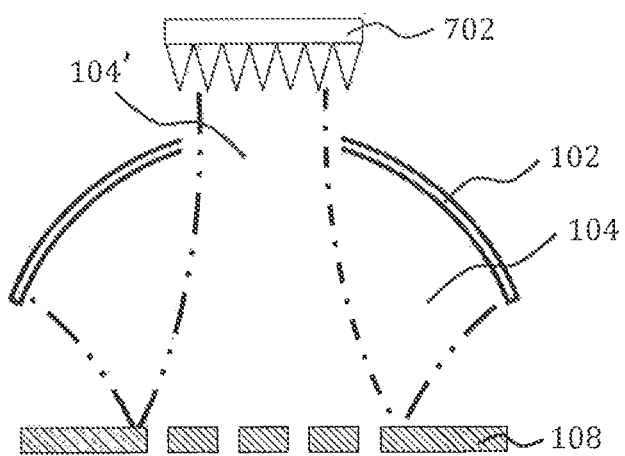
Figure 8:
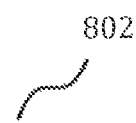

FIGS. 2B-E are a set of graphs each illustrating spatial pressure distributions, in accordance with various embodiments;

FIG. 2F is a plot illustrating transition depth versus frequency in accordance with various non-limiting embodiments;

FIG. 3 is a block diagram illustrating various methods and systems of ultrasound treatment, in accordance with various non-limiting embodiments;

FIG. 4 is a diagram illustrating set of different mask and transducer configurations, in accordance with various non-limiting embodiments;

FIG. 5 is a block diagram illustrating an exemplary ultrasound treatment system in accordance with various non-limiting embodiments;

FIG. 6 is a block diagram illustrating an exemplary ultrasound treatment system, in accordance with various non-limiting embodiments;

FIG. 7 is a block diagram illustrating an exemplary ultrasound treatment system in accordance with various non-limiting embodiments; and FIG. 8 is a spatio-temporal equation describing various ultrasound fields, in accordance with various non-limiting embodiments.

DESCRIPTION

The following description is merely exemplary in nature and is in no way intended to limit the various embodiments, their application, or uses. As used herein, the phrase "at least one of A, B, and C" should be construed to mean a logical (A or B or C), using a non-exclusive logical "or," As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices, in addition, the embodiments may be practiced in any number of industrial or medical contexts and that the various embodiments relating to a method and system for ultrasound treatment as described herein are merely indicative of exemplary applications for the invention. For example, the principles, features and methods discussed may be applied to any industrial or medical application. Further, various aspects of the various embodiments may be suitably applied to cosmetic applications. Moreover, some of the embodiments may be applied to cosmetic enhancement of skin and/or various subcutaneous tissue layers.

According to various embodiments described herein, methods are provided to create tailored space-time acoustic energy distributions in a treatment region. Various embodiments provide controlling delivery of acoustic energy into a treatment region by modulating an input energy distribution with a mask to create an output energy distribution. Since temperature in a targeted portion of a treatment region is proportional to the intensity of acoustic energy that is delivered, various embodiments provide controlling delivery acoustic energy into a treatment region which exceeds a threshold of cell death.

Various embodiments provide an ultrasound system configured for concentration of energy and increased power output to treat tissue in a region of interest. Some embodiments include an ultrasound system comprising a mask, which provides a greater intensity of ultrasound energy from the mask than the intensity the ultrasound intensity from the source. In some embodiments, the intensity of ultrasound energy at the mask can be tuned to different depths or sizes of lesions or shapes by tailoring the size of the aperture and the width of the mask. In some embodiments, the source is the primary source of ultrasound energy and the energy that is output of the mask is the secondary source of energy.

In some embodiments the mask can be cooled to control the tissue temperature in the region of interest. When using the ultrasound system at shallow depths in tissue, the coupling medium fills the apertures. In some embodiments, high-frequency can improve the targeting shallow depths within the tissues of the region of interest, in some embodiments, the primary source provides ultrasound energy to a mask comprising a plurality of apertures which converts the primary energy into a new energy field at the exit of each aperture, which is the secondary source, in some embodiments, the width of the mask can be thicker which can configure the aperture as a waveguide. In some embodiments, the thickness of the mask can tune the energy field of the secondary source.

In some embodiments, the mask may be shaped (i.e. not flat) and can be configured to focus energy to one point. In some embodiments, the ultrasound system comprising mask can create a lesion in a surface of skin. The mask can be configured to create a lesion at a surface of skin in a region of interest. In some embodiments, the ultrasound system can comprise a temperature modulator coupled to or integrated into mask and configured to modulate the temperature of the mask. For example, the temperature of the mask can be modulated using electric currents or Peltier modules. Modulating temperature of the mask can be used to configure the secondary source of energy for treatment of a surface of the skin. Modulating temperature of the mask can be configured for use of a photon-based energy source, which can be a tertiary source of energy. Typically, the mask will absorb acoustic or ultrasound energy such that the mass does not heat by absorbing the ultrasound energy.

Various embodiments provide methods and systems for concentrating sound energy source onto mask of apertures to produce treatment effects. In some embodiments, the apertures can yield greater power output than if aperture area was covered by a transducer alone. The apertures can be varied sizes and shapes to create treatment effects of varied sizes, depths, and shapes. In some embodiments, the acoustic energy can contain one or more frequencies to produce varied sizes, depths, and shapes of treatment.

In some embodiments, the apertures can include auxiliary components, such as, for example, thermal control components. In some embodiments, a coupling medium between sound energy source and mask can be liquid and include thermal, hydraulic, and/or pneumatic control. A liquid coupling medium can be dispensed through apertures to provide external coupling to treatment area. The coupling medium can be temperature controlled.

In some embodiments, the treatment effect can be a thermal effect in tissue in a region of interest. In some embodiments, a treatment effect can be a non-thermal effect in tissue in a region of interest. In some embodiments, a treatment effect can start below the surface or extend to the surface of skin. In some embodiments, sound energy and mask of apertures can vary in three dimensions and/or be time varying.

In some embodiments, the ultrasound treatment system can be combined with ultrasound imaging. In some embodiments, the ultrasound treatment system can be treatment system combined with other imaging, other sensing systems, and/or tissue parameter monitoring systems. In some embodiments, the ultrasound treatment system can be combined with a photon based, RF current, or other energy source.

Various embodiments provide a method for providing ultrasound treatment. In some embodiments, emitting primary ultrasound energy field from primary energy source; directing the primary ultrasound energy field into a plurality of apertures in a mask; converting the primary ultrasound energy field into a plurality of secondary ultrasound energy fields having an increased intensity; delivering the plurality of secondary ultrasound energy fields into a treatment region comprising the tissue; and initiating a thermal effect in the treatment region.

In some embodiments, the method can further comprise monitoring of results of the at least one treatment effect in the treatment region during the delivering the output energy. In some embodiments, the method can further comprise monitoring of results of the at least one treatment effect in the treatment region after the delivering the output energy. In some embodiments, the method can further comprise planning of additional treatment.

In some embodiments, the at least one treatment effect is a cosmetic enhancement. In some embodiments, the at least one treatment effect is at least one of coagulation, increased perfusion, reduction of inflammation, generation of heat shock proteins, and initiation of healing cascade. In some embodiments, the at least one treatment effect is peaking inflammation in the injury location and initiating a coagulation cascade in at least a portion of the treatment region. In some embodiments, the at least one treatment effect is stimulating collagen growth in a portion of treatment region. In some embodiments, the method can further comprising imaging the treatment region.

Various embodiments provide an ultrasound treatment system. In some embodiments, the system can comprise a primary energy source configured for delivery of primary ultrasound energy field; a mask configured to receive and convert the ultrasound energy into a secondary source configured to provide a secondary ultrasound energy field; and a control system for facilitating control of the primary energy source and the secondary energy source; wherein an intensity of the secondary ultrasound energy field is greater than the intensity of the primary ultrasound energy field.

In some embodiments, the mask comprising a plurality of apertures configured to convert the primary ultrasound energy field into the secondary ultrasound energy field. In some embodiments, the system can further comprise a temperature modulator coupled to the mask and operable to modulate a temperature of the mask.

In some embodiments, the system can further comprise a photon based energy source configured to deliver photon based energy through the secondary energy source and into the treatment region. In some embodiments, the system can further comprise a radio frequency based energy source configured to deliver radio frequency energy through the secondary energy source and into the treatment region. In some embodiments, the output energy is configured to initiate a treatment effect in the treatment region.

Various embodiments provide an ultrasound treatment system, in some embodiments, the system can comprise a primary energy source configured for delivery of primary ultrasound energy field; a mask configured to receive and convert the ultrasound energy into a secondary source configured to provide a secondary ultrasound energy field; and a control system for facilitating control of the primary energy source and the secondary energy source; wherein an intensity of the secondary ultrasound energy field is greater than the intensity of the primary ultrasound energy field.

In some embodiments the thermal effect is one of heating the tissue, or creating a conformal region of elevated temperature in the treatment region. In some embodiments, the thermal effect is one of lesion creation in the region of interest, tissue necrosis in a portion of the treatment region; coagulation tissue in the treatment region, or exceeding a thermal capacity of tissue in a portion of the treatment region, and combinations thereof.

In some embodiments, the method can comprise controlling at least one of the primary energy source and the secondary energy source. In some embodiments, the method can comprise delivering a photon-based energy into the treatment region and imitating a second treatment effect in the treatment region.

In some embodiments, a method can comprise localizing a treatment region; choosing a primary energy source, delivering acoustic input energy from a primary energy source through a plurality of mask apertures to create an output energy; delivering the output energy into the treatment region; and controlling the output energy to produce at least one treatment effect in the treatment region.

Figure 1:
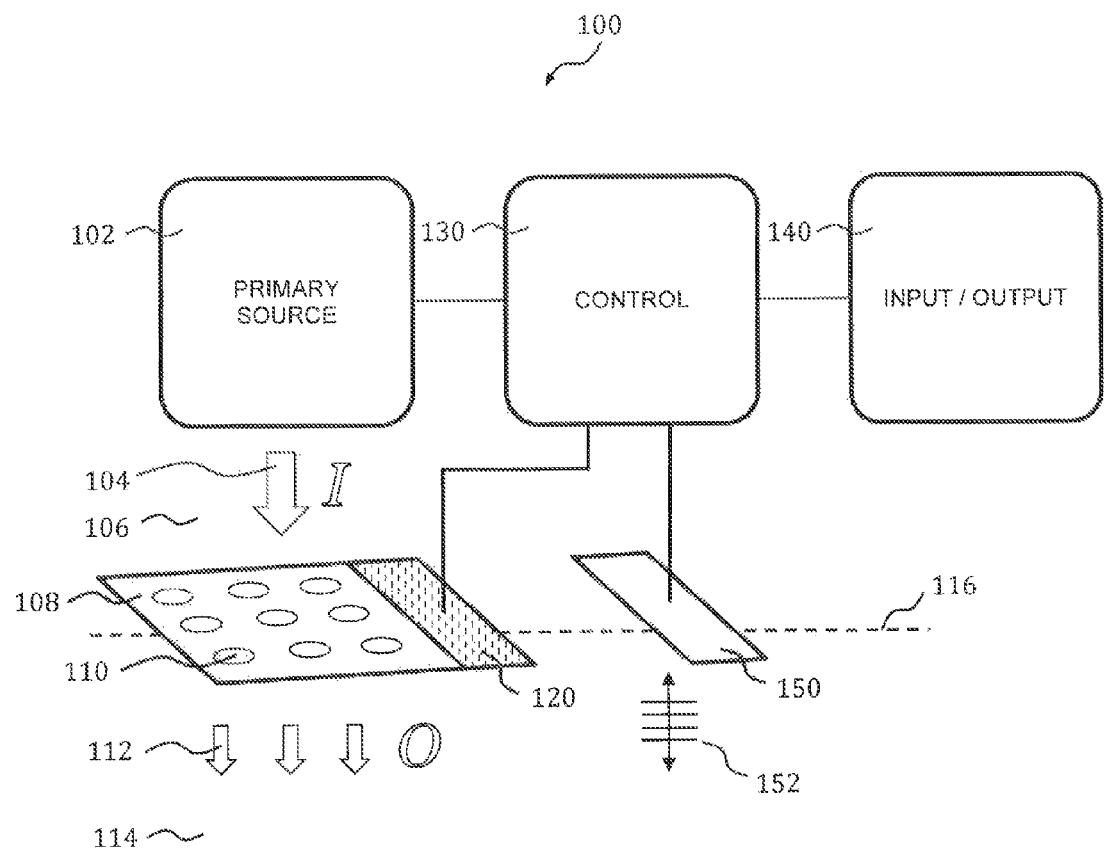
FIG. 1 is a block diagram illustrating an ultrasound treatment system and method, in accordance with various non-limiting embodiments.

With reference to FIG. 1, a method of ultrasound treatment is illustrated. In various embodiments, ultrasound treatment method can comprise localizing a primary energy source 102 and delivering input energy 104 through a coupling medium 106 onto a mask 108 and through apertures 110, which, acting as secondary sources create output energy 112 in a treatment region 114, after passing through potential layers 116. In some embodiments, mask components 120 are mounted upon, adjacent to, or disposed within mask 108 and include passive or active temperature control components. In some embodiments, mask 108 can comprise temperature sensors, contact sensors, pressure sensors, position tracking sensors including optical position sensors, impedance sensors, transducers, absorbers, reflectors, membranes, matching layers, fluid control, hydraulic, and pneumatic components to name a few. Primary energy source 102 and mask components 120 are controlled via control system 130, with associated software and methods. Control system 130 can comprise an input output (I/O) system 140, such as a touch panel, switches, indicators, and audible alarms. In some embodiments secondary systems 150 are also coupled to control system 130, and are configured for ultrasound imaging, therapy and/or monitoring 152, tissue parameter monitoring. In some embodiments, an additional energy source can provide laser or photon based therapies, radio frequency (RIF) based therapy. Control system 130 can coupled and/or control impedance monitoring, video monitoring, motion control, and can also include memory devices such as EEPROMs or rechargeable batteries and systems for a portable, hand-held, or wireless ultrasound treatment system. In various embodiments, primary energy source 102 is an ultrasound or other acoustic source. In various embodiments, primary energy source 102 can be composed of single or multiple element cylindrical, spherical, planar, lensed or electronically phased or unfocused acoustic sources or their combination in any geometric configuration, power amplitude, and timing, creating any spatial and temporal distribution of input energy 104. In various embodiments, ultrasound based primary energy source 102 is composed of lead zirconate titanate piezoelectric ceramics or other transducer materials such as lithium niobate. In various embodiments, coupling medium 106 is liquid. In various embodiments, coupling medium 106 is a gel. In various embodiments, coupling medium 106 is a solid. In various embodiments, coupling medium 106 is a gas. In various embodiments, coupling medium 106 is a composite material. In various embodiments, treatment region 114 (or region of interest) comprises a skin surface and subcutaneous tissue below. In various embodiments, treatment region 114 comprises an organ or artificial or engineered tissue. In various industrial embodiments, treatment region 114 can comprise plastic or other materials to be treated by output energy 112. In various embodiments, ultrasound treatment system and method are used extracorporally, in other embodiments, ultrasound treatment system and method are used intracorporally or both.

In various embodiments mask 108 is metal. In various embodiments mask 108 is a composite. In various embodiments, mask 108 is multilayered. In various embodiments, mask 108 can move manually or via motion mechanism or can be exchanged for other masks. In various embodiments, apertures 110 are holes. In various embodiments, coupling medium 106 is solid, apertures 110 are solid and conduct sound, and mask 108 is a void or composed of materials that otherwise do not conduct sound. In various embodiments, mask 108 is covered by a membrane. In various embodiments, apertures 110 are passive or active materials. In various embodiments, apertures 110 are flat or shaped, such as lensed. In various embodiments, apertures 110 are waveguides. In various embodiments, mask 108 partially transmits sound through potential layers 116 into treatment region 114. In various embodiments, mask 108 can absorb sound. In various embodiments, mask 108 can reflect, deflect, and/or diffuse some or all of input energy 104.

In various embodiments, output energy 112 creates a mechanical effect in treatment region 114. For example, a mechanical effect can be any one of or any combination of cavitation, vibration, hydrodynamic, resonance-induced, streaming, vibro-accoustic stimulation, or a pressure gradient. In various embodiments, output energy 112 creates an ablative effect in treatment region 114. For example, an ablative effect can be any one of or any combination of lesion creation, tissue necrosis, coagulation, or exceeding a thermal capacity of tissue, or combinations thereof. In various embodiments, output energy 112 creates a thermal effect in treatment region 114. For example, a thermal effect can be at least one of heating subcutaneous tissue, creating a conformal region of elevated temperature, or creating conformal region of elevated temperature and a second conformal region of elevated temperature, or combinations thereof.

In various embodiments, output energy 112 can trigger (initiate and/or stimulate) one or more bio-effects in treatment region 114. A biological effect can be stimulating or increase an amount of heat shock proteins. Such a biological effect can cause white blood cells to promote healing of a portion of subcutaneous tissue in treatment region 114. A biological effect can be to restart or accelerate the wound healing cascade in treatment region 114 and/or in tissue proximate thereto. A biological effect can be increasing the blood perfusion in treatment region 114 and/or in tissue proximate thereto. A biological effect can be encouraging collagen growth. A biological effect may increase the liberation of cytokines and may produce reactive changes in treatment region 114 and/or in tissue proximate thereto. A biological effect may by peaking inflammation in treatment region 114 and/or in tissue proximate thereto. A biological effect may at least partially shrinking collagen portion in treatment region 114 and/or in tissue proximate thereto. A biological effect may be denaturing of proteins in treatment region 114 and/or in tissue proximate thereto.

A biological effect may be creating immediate or delayed cell death (apoptosis) in treatment region 114 and/or in tissue proximate thereto. A biological effect may be collagen remodeling in treatment region 114 and/or in tissue proximate thereto. A biological effect may be the disruption or modification of biochemical cascades. A biological effect may be the production of new collagen. A biological effect may be a stimulation of cell growth in treatment region 114 and/or in tissue proximate thereto. A biological effect may be angiogenesis. A biological effect may be a cell permeability response. A biological effect may be an enhanced delivery of medicants to treatment region 114 and/or to tissue proximate thereto.

In various embodiments, output energy 112 can initiate and/or stimulate one or more biological responses in treatment region 114, such as, those described herein. For example, a biological response can be at least one of diathermy, hemostasis, revascularization, angiogenesis, growth of interconnective tissue, tissue reformation, ablation of existing tissue, protein synthesis and/or enhanced cell permeability.

With reference to FIG. 2A and according to various embodiments, an ultrasound treatment system, can comprise an input energy 104 of one or more wavelengths lambda, λ, incident on a mask 108, with apertures 110 of dimensions s per side, thereby creating an output energy 112 in the treatment region 114. Referring now to FIGS. 2B to 2E the spatial distribution of output energy 112, in the treatment region 114 is illustrated from a single aperture 110 as the side, s, of the aperture is increased from $\lambda/2$ to $\lambda$ to $2\lambda$ to $10\lambda$, respectively. For example, acoustically small apertures, i.e. $\lambda \le 1$, the lateral (along x or y) and axial (along z) normalized pressure magnitude follow a smooth and monotonic contour. However, for acoustically large apertures, $\lambda \le 1$, constructive and destructive acoustic interference in the treatment region 114 create a more complex output energy distribution, with an axial peak occurring near the so-called far-field transition distance, $s^2/4\lambda$, for a square aperture of side s, or $\alpha^2/\lambda$ for a circular aperture of radius $\alpha$. With reference to FIG. 2F, in various embodiments, mask 108, apertures 110, energy source 102, mask components 120, and control system 130 are configured to place the free-field maxima of output energy 112 at a desired depth in the treatment region 114. In various embodiments lensed apertures can further control the acoustic field spatial distribution in the treatment region 114.

Moving to FIG. 3, in some embodiments the input acoustic energy 104, mask 108, and apertures 110 create an output energy 112 creating a treatment effect 302, such as a thermal effect, whose depth 304 in the treatment region 114 is optionally modulated via mask components 120, such as temperature control components. In various embodiments, the desired treatment effect 302 can include the surface. In various embodiments, changing the frequency of input energy 104 is configured to move the position of treatment effect 302 and/or provide multiple depths of treatment effect 302. In various embodiments, mask 108 may include components such as a layers 108A, such as a membrane layer or other layers, with or without apertures 110, which may be used to retain a liquid coupling medium 106. In various embodiments layer 108A is a plastic film. In various embodiments, treatment effect 302 can occur at various angles with respect to mask 108 based on magnitude and phase of input energy 104 at aperture 110. In various embodiments at least one of treatment effect 302 can intersect in the treatment region 114.

Various embodiments of masks 108 and apertures 110 are illustrated in FIG. 4. Aperture 110A illustrates a large opening or mesh-like mask 108, while in contrast aperture 110B is more closed, with smaller apertures 110. In various embodiments the relative acoustic spacing between adjacent apertures 110 determines if their output energy 112 combines partially or fully in the treatment region 114 or can be considered as independent sound fields. In some embodiments, apertures 1100 are placed in a random spatial pattern, within bounds, as opposed to a rectilinear or other periodic pattern, and can used to obscure potential treatment side effects, such as temporary edema or erythema on the surface of skin. In various embodiments, mask 108 has multiple sized or shaped apertures, such as apertures 110D and 110D' which can create multiple patterns of output energy 112 in the treatment region 114. In various embodiments, at least two different diameter or sized apertures 110D and 110D' create two different depths of treatment. In various embodiments, at least two different diameter or sized apertures 1101 and 1101D" create two different sized treatment regions. In various embodiments, mask 108 can consist of a line of apertures 110E or multi-dimensional apertures 110F, such as slots, which can produce different field patterns of output energy 112 along different axes. In various embodiments, mask 402 can be split into more than one zone and secondary systems 150, can be integrated, such as a transducer for an ultrasound imaging and monitoring system. In various embodiments, transducer can be configured in-line along mask 402 or transverse or along the center of a mask 404.

According to various embodiments as illustrated in FIG. 5, the primary energy source 102 is a spherically focused or lensed ultrasound source, which concentrates acoustic input energy 104 emitted from a large surface area (e.g. a spherical shell) through an enclosed coupling, medium 106, such as water, onto a mask 108, such as a stainless steel mask, and through apertures 110, to create a pattern of output energy 112 in the treatment region 114. In such embodiments, the level of output energy 112 can be made very intense, even if emitted from a small aperture 110, and such intense sound levels can be exploited in the treatment region 114 for treatment effects 302 such as thermal effects. Such embodiments illustrate that even if the aperture 108 is physically small or acoustically small a large amount of power can be emitted at the aperture 110. Such large power output may not be easily deliverable if a single active transducer element was disposed at aperture 110. In various embodiments, a fluid coupling medium 106 can be held above atmospheric pressure or consist of a material that can avoid cavitation. In various embodiments, a fluid reservoir can be used to maintain the level of coupling medium 106. Various embodiments may be used to output fluid coupling medium 106 to provide external acoustic coupling to treatment region 114.

According to various embodiments and with reference to FIG. 6, the primary energy source is a cylindrically focused ultrasound source, which concentrates acoustic input energy 104 emitted from a large surface area (e.g. cylindrical shell) onto a mask 108 and through apertures 110, to create a pattern of output energy 112 in the treatment region 114. In various embodiments, the primary energy source is a phased array, including phase variation and/or beam steering, and including beamforming over the mask 108 and apertures 110.

According to various embodiments, as illustrated in FIG. 7, a primary energy source focuses an incident acoustic input energy 104 onto a mask 108, and a portion of such incident acoustic energy 104 is reflected back by such mask 108 as reflected input energy 104' which is then absorbed by an absorber 702. In one embodiment, an opening in the primary energy source can allow the reflected input energy 104' to pass through. In another embodiment, the absorber 702 is on the surface of or in front of the source. In another embodiment the primary source is electrically isolated where the reflected energy impinges on it, such electrically isolated region electronically damped by a network including a resistor, in another embodiment, opening in primary energy source 102 includes plastic tubing which absorbs and attenuates sound while serving as a liquid coupling fluid hydraulic control.

Moving to FIG. 8, a mathematical relationship 802 encapsulates the ultrasound treatment system as a spatio-temporal input energy 104 distribution function $I(x, y, z, t)$, which is modulated by a spatio-temporal aperture 110 mask 108 function $M(x, v, z, t)$ to create a spatio-temporal output energy 112 distribution function $O(x, y, z, t)$. As such, any acoustic field distribution and timing can be synthesized for the output energy function 112. Of note, in various embodiments mask surface can be three-dimensional and/or time varying.

In various embodiments, ultrasound treatment system 100 is an entire system capable of at least one of treating, imaging, or monitoring, before, during and after treatment, using at least one of acoustic energy and any other energy source, including for example laser, photon emission, and, or radio frequency energy. In one embodiment, ultrasound treatment system 100 comprises acoustic primary energy source 102, control system 130, and at least one other energy source, all encompassed in one unit.

Various embodiments provide a method for providing ultrasound treatment. The method can comprise localizing a treatment region 114, choosing a primary energy source 102, delivering acoustic input energy 104 from the primary energy source 102 through the mask 108 apertures 110 and into the treatment region 114, and controlling the output energy 112 to produce at least one treatment effect 302 in the treatment region 114. The method can further comprise monitoring of results of the ultrasound treatment during and/or after of the delivery of acoustic output energy 112. The method can further comprise planning of additional treatment. In some embodiments, the method is a method of cosmetic enhancement.

The method can comprise providing at least one bio-effect in the in at least one treatment region 114. The method can comprise destroying tissue in the at least one treatment region 114. The method can further comprise generating at least one biological effect in tissue proximate to the at least one treatment region 114. Control of one or more parameters of the output energy 112, defines the explicit shape of the treatment region 114 to affect ultrasound treatment. As will be apparent to those of ordinary skill in the art, output energy 112 can be employed in any method and/or system described herein. It should be appreciated that designated treatment effect 302 has a conformal volume that can be spatially and temporally controlled by ultrasound treatment system 100 and expanded in one or more conformal volumes. Such effect will produce one or more distinct zones of controlled and predictable parameters and dimensions by either electronic and/or mechanical displacements of the acoustic primary energy source, 102 and associated components, mask 108, etc.

As used herein, the term cosmetic enhancement can refer to procedures, which are not medically necessary and are used to improve or change the appearance of a portion of the body. For example, a cosmetic enhancement can be a procedure that is used to improve or change the appearance of a nose, eyes, eyebrows and/or other facial features, or to improve or change the appearance and/or the texture and/or the elasticity of skin, or to improve or change the appearance of a mark or scar on a skin surface, or to improve or change the appearance and/or the content of fat near a skin surface, or the targeting of a gland to improve or change the appearance a portion of the body. Since it is not medically indicated for improving one's physical well-being, cosmetic enhancement is an elective procedure. As used herein, cosmetic enhancement does not diagnose, prevent, treat, or cure a disease or other medical condition. Furthermore, cosmetic enhancement is not a method for treatment of the human or animal body by surgery or therapy and diagnostic methods practiced on the human or animal body. Cosmetic enhancement is a non-surgical and non-invasive procedure. In some embodiments, cosmetic enhancement can be a non-surgical and non-invasive procedure that is performed at home by a user who is not a medical professional.

The following patents and patent applications are incorporated by reference: US Patent Application Publication No. 20050256406, entitled "Method and System for Controlled Scanning, Imaging, and/or Therapy" published Nov. 17, 2005; US Patent Application Publication No, 20060058664, entitled "System and Method for Variable Depth Ultrasound Treatment" published Mar. 16, 2006; US Patent Application Publication No. 20060084891, entitled "Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonic System", issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; and US Patent Application Publication No, 20080281255, entitled "Methods and Systems for Modulating Medicants Using Acoustic Energy" published Nov. 13, 2008.

While the invention has been disclosed herein, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are not intended to be limiting in describing the full scope of systems and methods of this invention. Equivalent changes, modifications and variations of various embodiments, materials, systems, and methods may be made within the scope of the present invention, with substantially similar results.

The invention claimed is:

1. A method for treating tissue with ultrasound energy, the method comprising;
   emitting ultrasound energy from primary energy source;
   directing the ultrasound energy into a plurality of apertures in a secondary energy source, wherein the plurality of apertures in the secondary energy source are not equivalent, wherein a first group of the plurality of apertures is configured to deliver a first group of the plurality of energy fields to a first depth in the treatment region and a second group of the plurality of apertures is configured to deliver a second group of the plurality of energy fields to a second depth in the treatment region, wherein the first depth is different than the second depth;
   converting the ultrasound energy into a plurality of energy fields having an increased intensity than the primary energy source;
   delivering the plurality of energy fields into a treatment region comprising the tissue; and
   initiating a thermal effect in the treatment region.

2. The method according to claim 1, wherein the thermal effect is one of heating the tissue, and creating a conformal region of elevated temperature m the treatment region.

3. The method according to claim 1, wherein the thermal effect is one of lesion creation in the region of interest, tissue necrosis in a portion of the treatment region; coagulation of tissue in the treatment region, and exceeding a thermal capacity of tissue in a portion of the treatment region.

4. The method according to claim 1, further comprising controlling at least one of the primary energy source and the secondary energy source.

5. The method according to claim 1, further comprising delivering a photon-based energy into the treatment region and initiating a second treatment effect in the treatment region.

6. The method according to claim 1, further comprising delivering radio frequency energy through the secondary energy source and into the treatment region and initiating a second treatment effect in the treatment region.

7. The method according to claim 1, further comprising controlling a temperature modulator coupled to the secondary energy source and operable to modulate a temperature of the secondary energy source.

8. The method according to claim 1, further comprising imaging at least a portion of the treatment region.

9. The method according to claim 1, further comprise monitoring of at least one of the delivering the plurality of energy fields into a treatment region comprising the tissue and the initiating a thermal effect in the treatment region.

10. The method according to claim 1, wherein the thermal effect initiates peaking inflammation in the injury location and a coagulation cascade in at least a portion of the treatment region.

11. The method according to claim 1, wherein the thermal effect initiates stimulation of collagen growth in a portion of the treatment region.

12. The method according to claim 1, wherein the first group of the plurality of apertures is configured to form a first group of shaped conformal regions of elevated temperature in the treatment region and the second group of the plurality of apertures is configured to form a second group of shaped conformal regions of elevated temperature in the treatment region, wherein the first group of shaped conformal regions of elevated temperature comprise a different volumetric shape than the second group of shaped conformal regions of elevated temperature.

13. A method for providing ultrasound treatment to tissue, the method comprising:
   targeting a treatment region comprising tissue;
   choosing a primary energy source,
   directing an acoustic input energy from a primary energy source through a plurality of mask apertures, wherein the plurality of mask apertures are not equivalent, wherein a first group of the plurality of apertures is configured to form a first group of shaped conformal regions of elevated temperature in the treatment region and a second group of the plurality of apertures is configured to form a second group of shaped conformal regions of elevated temperature in the treatment region, wherein the first group of shaped conformal regions of elevated temperature comprise a different volumetric shape than the second group of shaped conformal regions of elevated temperature;
   creating an acoustic output energy comprising a plurality of ultrasound fields, each having an increased intensity as compared to the input energy;
   delivering the output energy into a plurality of locations in the treatment region; and
   producing a treatment effect on at least a portion of tissue in the treatment region.

14. The method according to claim 13, wherein the treatment effect on the tissue is at least one of coagulation, increased perfusion, reduction of inflammation, generation of heat shock proteins, and initiation of healing cascade.

15. The method according to claim 13, wherein the treatment effect on tissue is peaking inflammation in the tissue at an injury location and initiating a coagulation cascade in at least a portion of the tissue in the injury location.

16. The method according to claim 13, wherein the treatment effect is stimulating collagen growth in a portion of the tissue in the treatment region.

17. The method according to claim 13, wherein the treatment effect is one of lesion creation in the region of interest, tissue necrosis in a portion of the treatment region; coagulation of a portion of the tissue in the treatment region, and exceeding a thermal capacity of the tissue in a portion of the treatment region.

18. The method according to claim 13, further comprising imaging at least a portion of the treatment region.

* * * * *